United States Patent [19]
Meginniss, III et al.

[11] Patent Number: 5,815,872
[45] Date of Patent: Oct. 6, 1998

[54] PRESSURE OVERLOAD INDICATOR SYSTEM FOR POWER TOOTHBRUSHES

[75] Inventors: Stephen M. Meginniss, III, Seattle; Kent E. Plant, Jr., Bellevue; Matthew D. Bixby, Seattle; David Giuliani, Mercer Island, all of Wash.

[73] Assignee: Optiva Corporation, Bellevue, Wash.

[21] Appl. No.: 907,756

[22] Filed: Aug. 8, 1997

[51] Int. Cl.⁶ .......................... A46B 13/02; A46B 15/00; A61C 17/22
[52] U.S. Cl. .............................. 15/22.1; 15/105; 15/167.1
[58] Field of Search .................... 15/22.1, 105, 167.1

[56] References Cited

U.S. PATENT DOCUMENTS

| | | | |
|---|---|---|---|
| 4,253,212 | 3/1981 | Fujita | 15/167.1 |
| 4,450,599 | 5/1984 | Scheller et al. | 15/22.1 |
| 4,476,604 | 10/1984 | White et al. | 15/105 |
| 4,679,271 | 7/1987 | Field et al. | 15/52.1 |
| 4,680,825 | 7/1987 | White et al. | 15/105 |
| 4,698,869 | 10/1987 | Mierau et al. | 15/105 X |
| 4,716,614 | 1/1988 | Jones et al. | 15/105 |
| 4,744,124 | 5/1988 | Wang et al. | 15/105 |
| 4,766,432 | 8/1988 | Field et al. | 340/825.17 |
| 5,146,645 | 9/1992 | Dirksing | 15/167.1 |
| 5,214,819 | 6/1993 | Kirchner | 15/22.1 |
| 5,282,291 | 2/1994 | Spieler et al. | 15/105 X |
| 5,315,732 | 5/1994 | Huefner et al. | 15/167.1 |
| 5,331,707 | 7/1994 | Irizarry | 15/167.1 |
| 5,355,544 | 10/1994 | Dirksing | 15/105 |
| 5,398,369 | 3/1995 | Heinzelman et al. | 15/167.1 |
| 5,493,747 | 2/1996 | Inakagata et al. | 15/22.1 |
| 5,502,861 | 4/1996 | Spieler et al. | 15/167.1 |
| 5,561,881 | 10/1996 | Klinger et al. | 15/22.1 |

FOREIGN PATENT DOCUMENTS

| | | | |
|---|---|---|---|
| 481553 | 4/1992 | European Pat. Off. | 15/22.1 |
| 2471757 | 6/1981 | France | 15/167.1 |
| 3724476 | 7/1987 | Germany . | |
| 3716490 | 11/1988 | Germany | 15/105 |
| 4319615 | 6/1993 | Germany . | |
| 3-191905 | 8/1991 | Japan . | |
| 5-329024 | 9/1993 | Japan . | |
| 6-237014 | 9/1993 | Japan | 15/22.1 |
| 5-329024 | 12/1993 | Japan | 15/22.1 |
| 609238 | 2/1979 | Switzerland | 15/22.1 |
| 92/02159 | 2/1992 | WIPO . | |
| 92/10979 | 7/1992 | WIPO . | |
| 92/13499 | 8/1992 | WIPO . | |
| 92/20256 | 11/1992 | WIPO . | |
| 94/05229 | 3/1994 | WIPO . | |
| 94/09675 | 5/1994 | WIPO . | |

*Primary Examiner*—Mark Spisich
*Attorney, Agent, or Firm*—Jensen & Puntigam, P.S.

[57] ABSTRACT

A power toothbrush has a brushhead mounted at one end thereof, the brushhead including a base mounting element for bristles which extend from one surface thereof. Extending from the opposing surface of the base mounting element is a pressure contact member. A substantially rigid brushhead shield extends along and is adjacent to the opposing surface of the brushhead. The brushhead has a hinge-like portion which permits the brushhead to move or swivel in response to pressure being placed on the brushhead, while the brushhead is moving back and forth at its operating frequency of its normal brushing action at over 150 Hz. Thin electrical switch contacts, which are part of an electrical circuit, are positioned on the brush shield, spaced from the contact member on the brushhead. When sufficient pressure is applied against the brushhead, the brushhead moves sufficiently about the hinge, while also continuing to move in normal action that the pressure contact member comes into contact with and then closes the switch contacts, closing the electrical circuit and resulting in a visual indication that the brushhead pressure has exceeded the maximum limit for desirable brushing pressure.

25 Claims, 6 Drawing Sheets

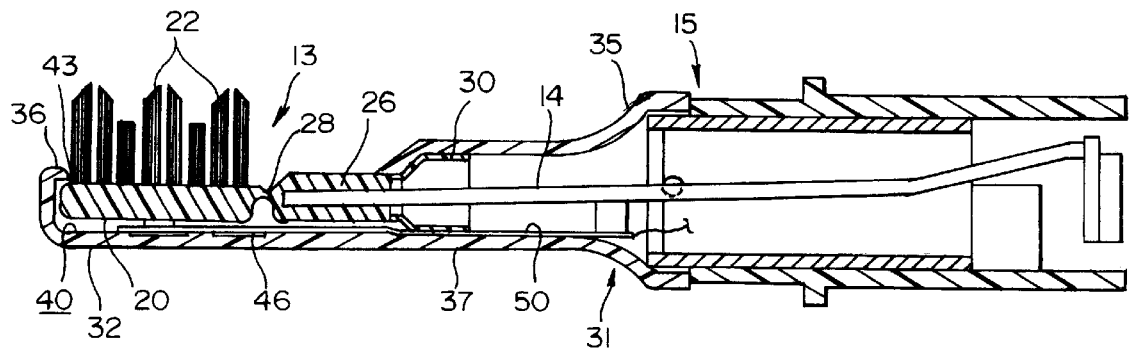
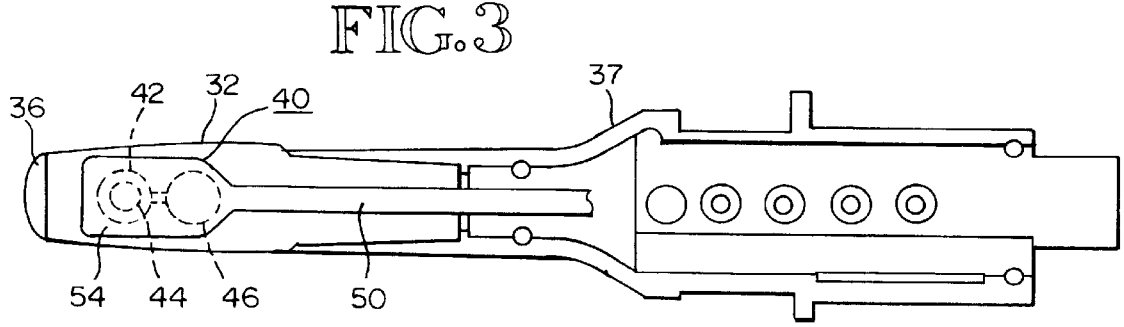
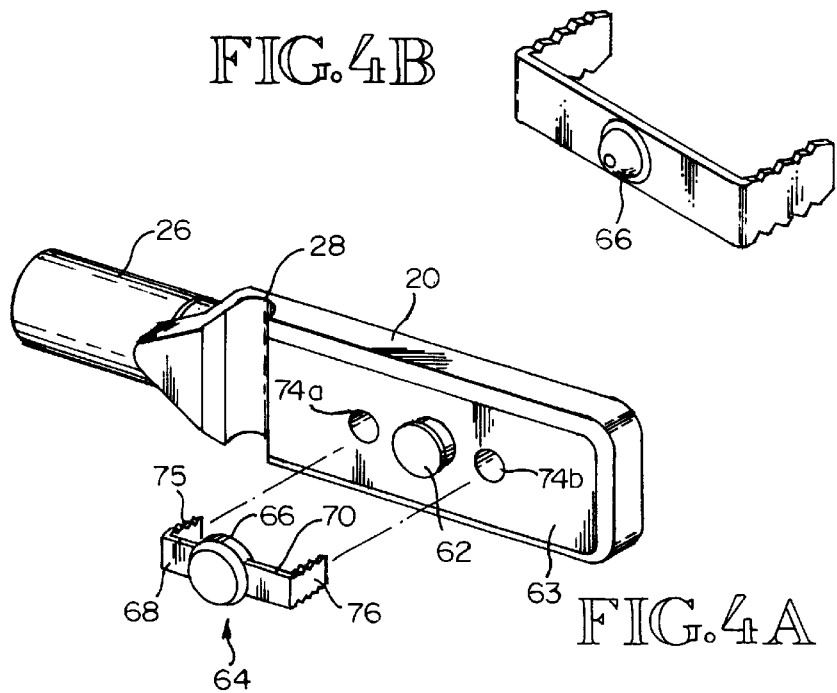

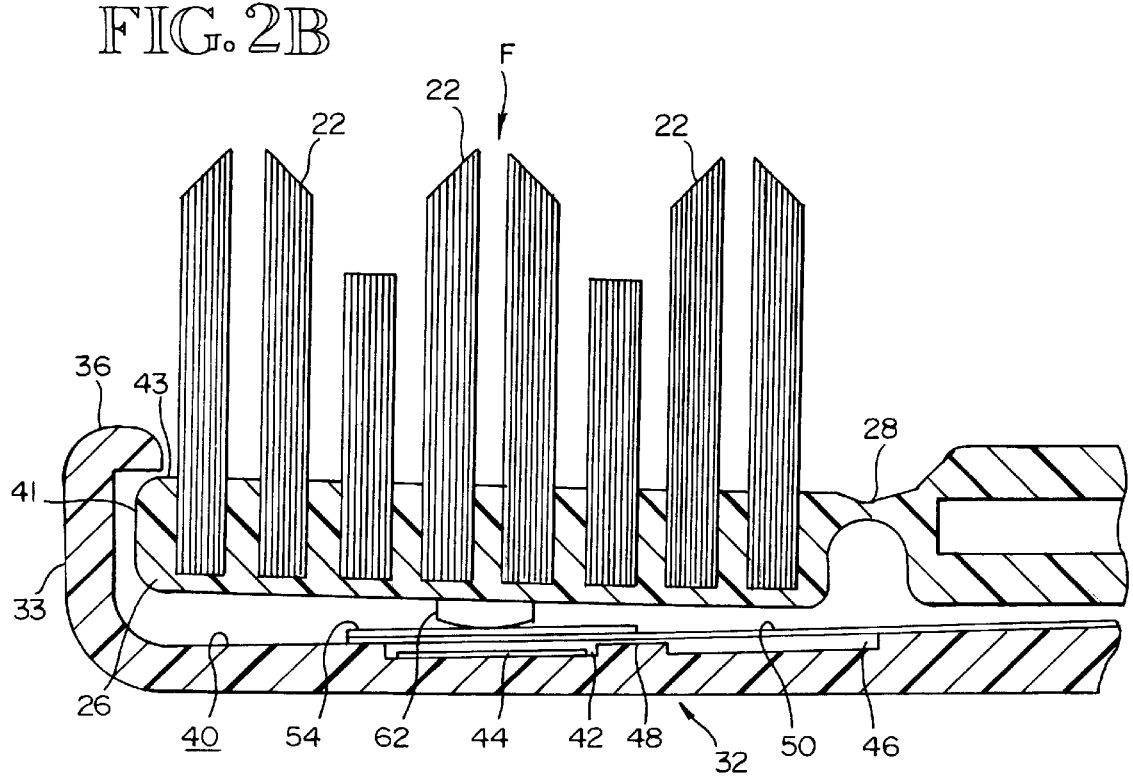
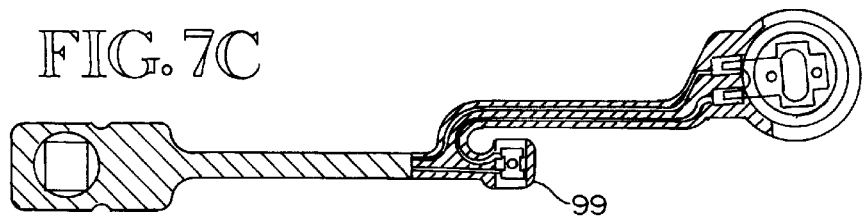
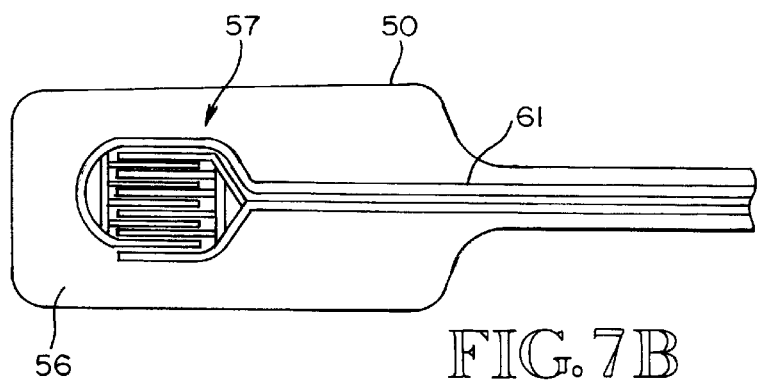

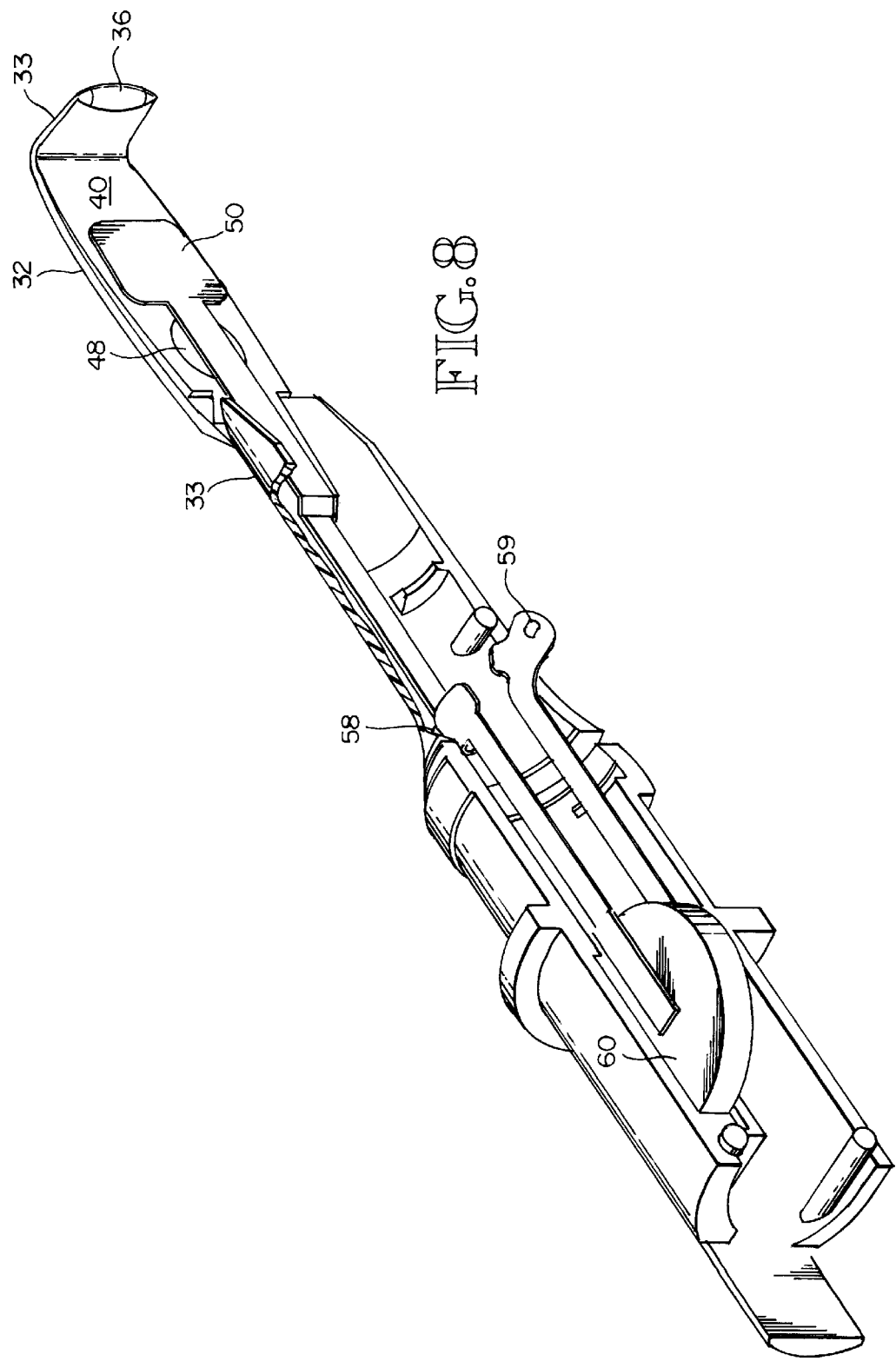

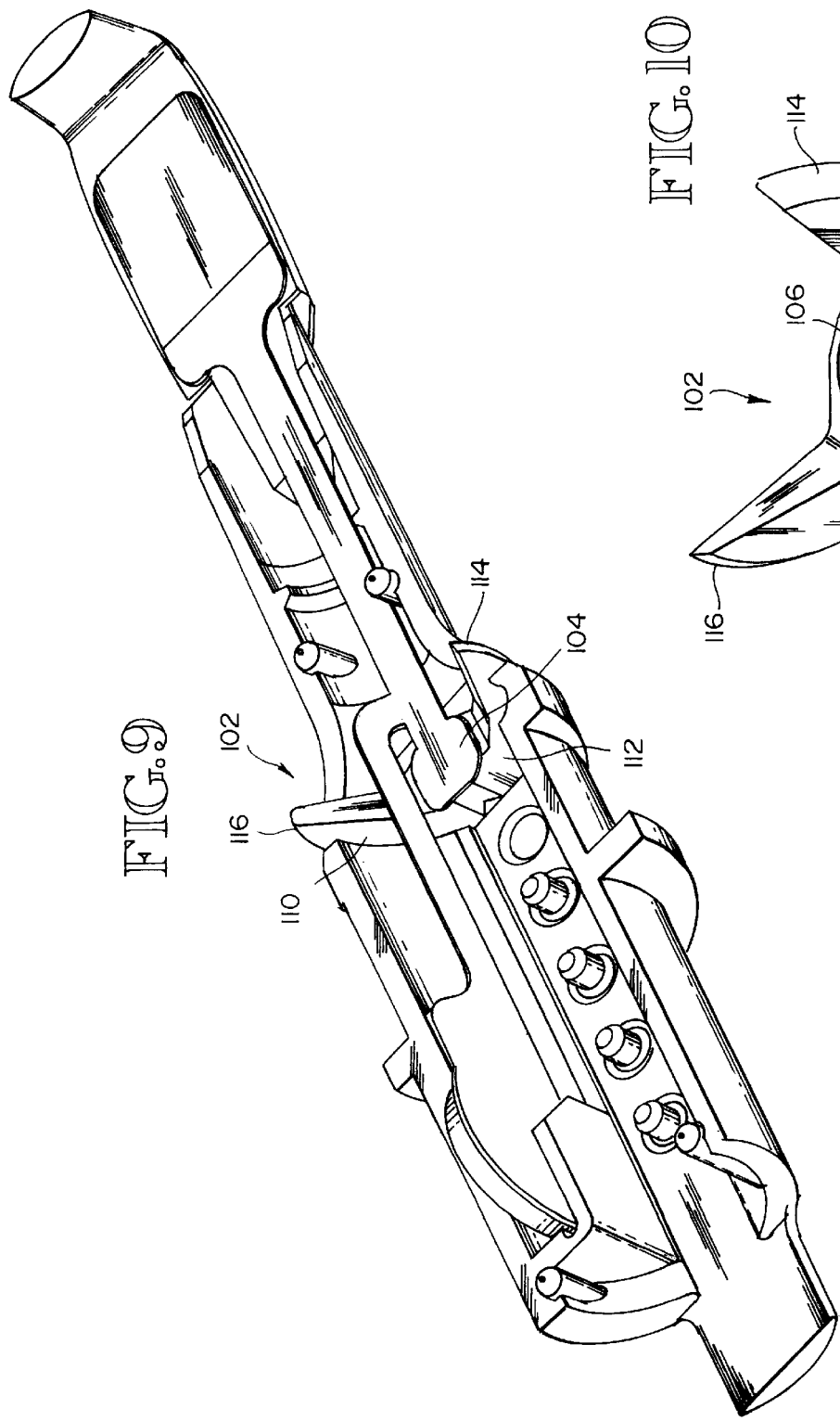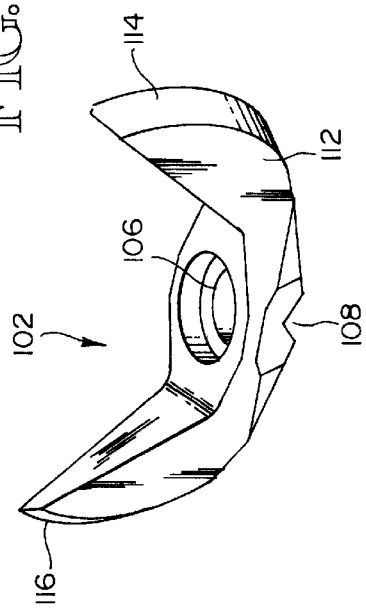

5,815,872

PRESSURE OVERLOAD INDICATOR SYSTEM FOR POWER TOOTHBRUSHES

TECHNICAL FIELD

This invention relates generally to power toothbrushes, and more specifically concerns a system for determining when the toothbrush is being overloaded with pressure applied by the user to the toothbrush against the teeth, and then providing a recognizable indication thereof to the user.

BACKGROUND OF THE INVENTION

During recent years, dental professionals have become increasingly concerned over the effects of abrasion caused by hard brushing of the teeth. A substantial percentage of people have incurred damage to their gums and sometimes even the enamel on their teeth by either using toothbrushes with bristles which are too stiff, or by applying too much pressure on the toothbrush against the teeth (hard brushing).

In response to these concerns, there has been an increasing educational effort directed toward brushing teeth with an appropriate amount of force, as well as a significant emphasis on using softer bristles. Most bristles are now in either "soft" or "extra soft" categories. Some power toothbrushes, moreover, have a particular potential for causing abrasion. Specific instructions are usually provided to the user of a power toothbrush concerning proper pressure levels.

A proper pressure range is important for another reason for power toothbrushes, including those which operate at frequencies in the "sonic" frequency range, particularly above 150 Hz. With such power toothbrushes, only a light pressure is necessary in order to gain maximum dental effect. The dental effect of such toothbrushes decreases significantly when too much pressure is applied. Unfortunately, however, in many cases, pressure well above that recommended by the manufacturer can be applied before the user becomes aware that the brush strokes of the power toothbrush are slowing down and the toothbrush is hence losing effect. With the particular toothbrush manufactured by the assignee of the present invention, for instance, a pressure of approximately 120 grams is appropriate. This is quite light and is almost akin to "skimming" the bristles over the teeth.

There are a large number of patents which are directed toward pressure sensing mechanisms of various kinds for toothbrushes. One such patent is U.S. Pat. No. 4,698,869, in which the brush must move back about one-half to one inch to activate the pressure sensor circuit. Other relevant recent patents include U.S. Pat. Nos. 5,282,291 and 5,502,861.

However, none of those references teach a reliable pressure sensor which directly measures the actual pressure applied on the brush against the teeth. Further, with many of the devices, the pressure indication is affected by the interior surface of the mouth pressing in against the brush.

DISCLOSURE OF THE INVENTION

Accordingly, the present invention is a pressure overload indication system for power toothbrushes, comprising: a brushhead member having a mounting base for bristles which extend from one surface thereof; a substantially rigid brushhead shield member which is positioned apart from the brushhead member when there is no pressure applied to the brushhead; pressure-sensing means positioned between the brushhead member and the brushhead shield; a hinge-like member supporting the brushhead at an inboard end thereof which allows the brushhead to move toward the brushhead shield member when pressure is applied against the teeth, acting on the pressure-sensing means; and means for indicating when the pressure sensed by the pressure-sensing means exceeds a predetermined value.

BRIEF DESCRIPTION OF THE DRAWINGS

FIGS. 2A and 2B are cross-section views showing a portion of the brush of FIG. 1.

FIG. 3 is a top plan view showing a portion of the brushhead housing of the system of FIG. 1.

FIG. 4A is an elevational view showing a brushhead contact member portion of the present invention.

FIG. 4B is an elevational view showing an alternative embodiment of a portion of FIG. 4A.

FIG. 7B is an enlarged view of a portion of FIG. 7A.

FIG. 7C is a plan view of a flexible switch circuit with just one LED.

FIG. 8 is a top plan view showing how the flexible switch circuit of FIG. 7A fits into the brush portion of the apparatus of FIG. 1.

FIG. 9 is a top plan view of a flexible switch circuit showing an alternative light mechanism (light guide) for indicating pressure overload.

FIG. 10 is a perspective view of the light guide of FIG. 9.

BEST MODE FOR CARRYING OUT THE INVENTION

Figure 1:
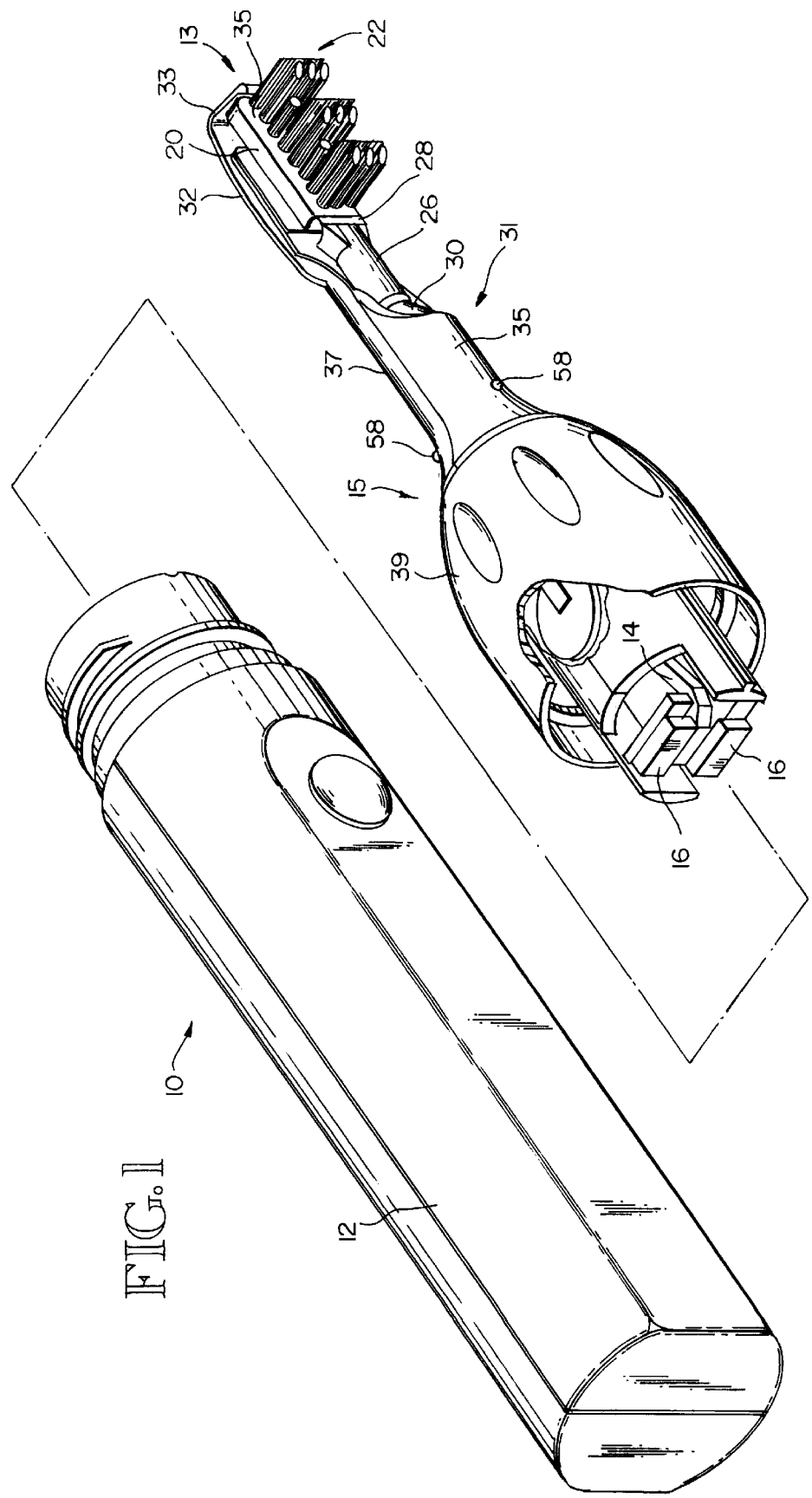
FIG. 1 is an exploded perspective view of a power toothbrush using the overload indication system of the present invention.

FIGS. 1 and 2 show an electronic power toothbrush, generally at 10, which is similar to that currently produced by the assignee of the present invention. It operates in the sonic frequency range, at approximately 31,000 separate strokes per minute, i.e. the brushhead moves back and forth (two brush strokes), through one complete cycle, approximately 15,500 times per minute. It should be understood, however, that FIG. 1 is illustrative of one power toothbrush and that the present invention may be used with power toothbrushes of other configurations and frequencies.

Toothbrush 10 includes a handle portion 12 in which is located a drive circuit for the brushhead and batteries to provide power for the drive circuitry. This particular toothbrush is described in more detail in U.S. Pat. No. 5,189,751 titled VIBRATING TOOTHBRUSH USING A MAGNETIC DRIVER and U.S. Pat. No. 5,378,153 titled HIGH PERFORMANCE ACOUSTICAL CLEANING APPARATUS FOR TEETH, both of which are owned by the assignee of the present invention and the contents of which are incorporated by reference herein.

A brushhead 13 extends from a lever arm 14 which is pivotally mounted in a brush portion 15 which is separable as a unit from handle portion 12. At the lower end of lever arm 14 are a pair of magnets 16 which are alternately attracted and repulsed by an electromagnetic drive circuit (not shown) in handle 12. As discussed above, the drive circuit is arranged to provide a brushhead frequency of approximately 15,500 cycles (a cycle is one complete sweep—back and forth) per minute. Again, however, this particular arrangement is for illustration of the present invention only, and is intended to have no limiting effect on the invention, which can be used with a wide variety of toothbrush designs and frequencies. It is possible for the present invention to be used even on a manual toothbrush, although power toothbrushes are the most significant application.

As indicated above, lever arm 14 is mounted for vibration, with brushhead 13 being mounted at the free end of the lever arm. Brushhead 13 includes a base portion 20 which is typically made from a polypropylene plastic, in which are mounted a series of bristle sections or tufts 22—22. The bristle tufts 22 are typically arranged in rows and columns and may be made from a variety of materials, including, for instance, nylon. The particular arrangement and configuration and material of the bristles, however, is not significant relative to the present invention.

Adjacent the inboard end of base 20 in the present invention is a brushhead support member 26, which is connected at one end to base 20 through a narrow "living" hinge 28. Typically, hinge 28 is 0.008–0.02 inches thick and is molded as a unitary part with brushhead base 20 and brushhead support member 26. In the embodiment shown, polypropylene is the material used for the hinge. Due to the alignment of the long molecular chains of the material produced during the molding process, the hinge is quite strong and difficult to crack or tear.

The other end of brushhead support member 26 is secured to the end of lever arm 14. A rubber seal assembly 30 seals the lever arm to an interior surface of a housing portion 31 of brush portion 15 of the toothbrush. The "living" hinge 28 is an important aspect of the present invention, as it permits brushhead base 20 to swivel or rotate thereabout upon pressure being applied by the user on the toothbrush to the teeth. Only a very low bending force is necessary to move the brushhead about hinge 28.

Housing 31 comprises upper and lower half sections 35, 37, which are welded together ultrasonically to produce the rigidity necessary for the structure to withstand the vibrating operation of the brush. Housing 31 in the embodiment shown is made from a very rigid plastic material such as ABS. Extending around a portion of housing 31 at the lower end thereof is a large retaining "nut" 39. Nut 39 is internally threaded and mates with a threaded portion of handle 12, solidly joining the two portions (handle portion 12 and brush portion 15) together. The interior of the upper end of nut 39 lies adjacent the exterior surface of housing 31.

FIGS. 1, 2, and 3 show a brush shield portion 32 of housing 31. Brush shield 32 is an extension of lower half section 37 of housing 31 and extends from a point beneath brushhead support member 26 to a point just past the outboard end of base section 20. Brush shield 32 has a length of approximately one inch and a width of approximately one-half inch. Since it is a part of lower half section 37, it is substantially rigid and does not bend under pressure. Shield 32 is flat underneath the brushhead. A free end portion 33 of shield 32 extends around the outboard end 41 of the base section 20 of the brushhead, and includes a lip portion 36 which overlays slightly the upper surface 43 of base section 20 at the outboard end thereof, to prevent significant movement of the brushhead in the direction away from brush shield 32. This protects hinge 28 from being bent in the opposite direction to that caused by normal pressure on the toothbrush. As indicated above, brush shield 32 is rigid and does not move or bend during normal operation. This is important to achieving an accurate pressure measurement, as discussed more fully below.

In the inner surface 40 of brush shield 32 (FIG. 3), located approximately central of base 20, is a recess 42. In the embodiment shown, recess 42 contains an electrical shorting dot 44. Shorting dot 44 in the embodiment shown is approximately 0.25 inches in diameter and approximately 0.005 inches thick (these dimensions can be varied), comprising a Mylar lower portion with an electrically conductive silver ink layer on the top thereof. Shorting dot 44 is secured to the bottom surface of recess 42 by a layer of pressure sensitive adhesive (PSA). Alternatively, a silver ink dot could be printed directly into the recess area.

Recess 42 is connected to an adjacent vent chamber recess 46 by a vent passage 48. Vent chamber 46 is similar in configuration to recess 42, having a depth of approximately 0.025 inches and a diameter of approximately 0.27 inches (which can also be varied). Vent chamber 46 allows a contact to be made between a flexible switch circuit member (explained in detail below), which overlays recess 42 and the shorting dot without a buildup of pressure within recess 42. In the embodiment shown, vent chamber 46 has about 4–5 times the unoccupied volume of switch recess 42. In the embodiment shown, vent passage 48 is a groove which is approximately 0.02 inches deep and approximately 0.04 inches wide.

Figure 5:
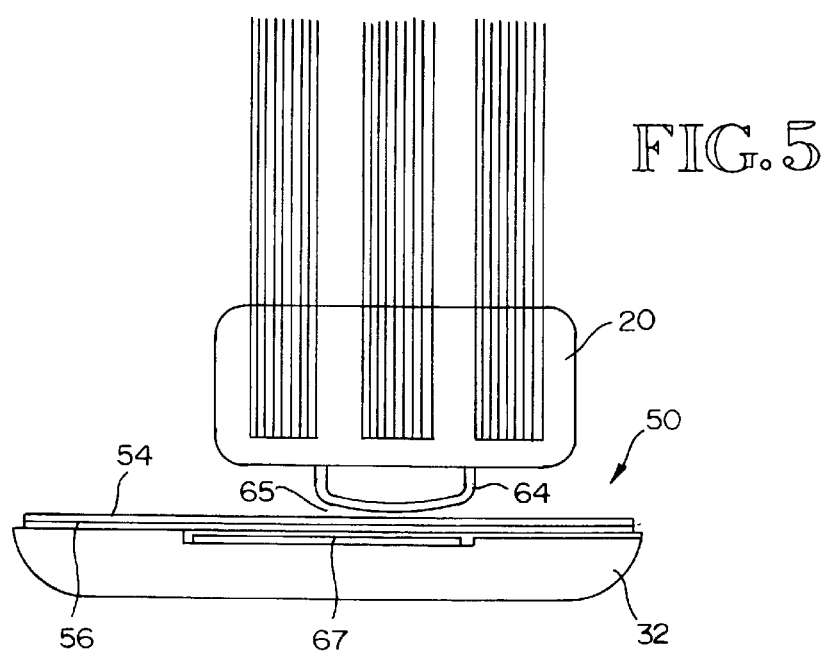
FIG. 5 is a simplified cross sectional view showing the contact sensor portion of the system of FIG. 4, the contact sensor being in a non-contact position.
Figure 6:
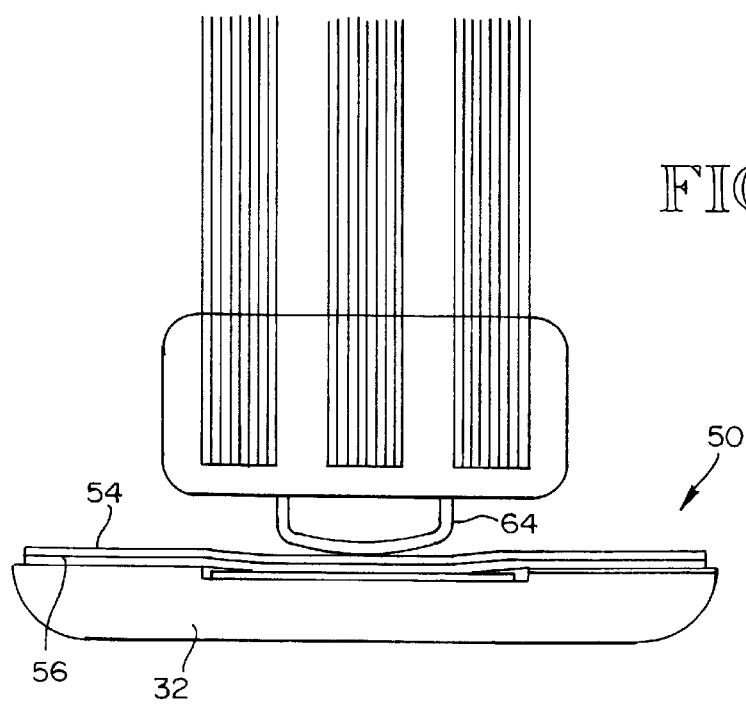
FIG. 6 is a view similar to that of FIG. 5 showing the contact sensor in a contact position.

Overlaying recess 42 and vent chamber 46 and extending into housing 31 is a flexible circuit 50 which includes a battery and two light emitting diodes (LEDs). Flex circuit 50 (FIGS. 5, 6 and 7) in the embodiment shown comprises a 0.005 base layer of Mylar polyester film 56 and an electrically conductive circuit positioned on the lower surface of Mylar layer 56, comprising a switch pattern 57, which is located over recess 42, LEDs 58 and 59, battery 60, and electrically conductive connecting lines or traces 61 connecting those elements together. A section of Tefzel (a low friction/wear resistant, flexible plastic material) approximately 0.005 inches thick is mounted to the upper surface of the Mylar layer (by a layer of PSA) over the area defined by the switch pattern 57.

Flex circuit 50 is sealed by PSA to upper surface 40 of brush shield 32, except for the area over recess 42 and vent chamber 46, to a point slightly past seal 30. The silver ink switch pattern portion 57 in the embodiment shown is located at the end of the flexible circuit and is in the form of interdigitated fingers, aligned with the length dimension of the brush shield. There is ordinarily no electrical contact between the fingers, so the electrical circuit is normally open. The particular arrangement of switch pattern 57 is shown in FIG. 7B. When the flex circuit is properly positioned in the brush housing 31, the switch pattern portion 57 is positioned directly over shorting dot 44 in recess 42. The flexible circuit, including the conductive members on the bottom of the Mylar layer, is sealed and made waterproof by a layer of PSA to the brush shield surface except for the area of the switch pattern 57, which must be able to make good electrical contact with shorting dot 44. The sealing of the remainder of the flexible circuit is discussed below.

In the embodiment shown, there is normally a space, referred to as a switch gap, of about 0.007 inches between switch pattern 57 and dot 44. The switch gap is selected such that approximately 150 grams of pressure (for the embodiment shown) applied on the brushhead, centered on button 62, while the apparatus is operating, is required to move the brushhead sufficiently that nubbin 64 first makes contact with the flex circuit and then bends that portion of the flex circuit sufficiently that switch pattern 57 makes electrical contact with shorting dot 44. In FIG. 2B, a resultant force F is shown centered on the middle tufts and button 62. If in operation, the resultant force is more outboard, the required contact pressure will be less than 150 grams, while if the resultant force is more inboard, the required contact pressure will be greater than 150 grams. Approximately 40 grams of pressure is needed to move the brushhead about hinge 28 sufficiently to cause a contact element portion of the brushhead to move through a first gap or distance 65 (FIG. 5) to make contact with the flex circuit and an additional 110 grams is required to move the brushhead sufficiently further that the flexible circuit is moved through a second gap or distance 67 into contact with the shorting dot 44. Different switch gaps, of course, will be necessary for different desired pressures and different flex circuit materials. In some applications, the first distance 65 can be zero.

Referring to FIG. 4A, the contact element portion of the brushhead which contacts switch pattern 57 is a button 62 which extends from a lower surface 63 of base 20 of the brushhead. In the embodiment shown, button 62 comprises an extending molded part of base portion 20 with a stainless steel cover or nubbin 64. The stainless steel nubbin 64 is generally in the form of a staple. Other configurations, of course, are possible. FIGS. 4A and 4B show alternative versions of the nubbin. In FIG. 4B there is no extending molded part on the brushhead. In both embodiments shown, the nubbin includes a circular cap portion 66 (FIG. 4B is smaller) which in the FIG. 4A embodiment fits over the molded button portion on the brushhead, and two opposing side portions 68 and 70 which extend outwardly from cap portion 66.

Extending at right angles from the outboard ends of side portions 68 and 70 are two wing portions 75 and 76. The wing portions include serrated or "wavy" edges which extend through openings 74a, 74b in brushhead base 20 in such a manner as to produce an interference fit. The "memory" of the plastic comprising base 20 results in the plastic material flowing into the wavy edges of the wing portions 75, 76, holding cover 64 firmly in place against the base of the brush. Because of this arrangement, there is no risk of cover 64 being pulled out of the brushhead during normal use.

In operation, when the brushhead is inserted into the mouth and the user applies pressure to the brush against the teeth, brushhead 13 swivels slightly toward brush shield 32 about hinge 28. As the brushhead continues to move (swivel) under increasing pressure, nubbin 64 makes contact with the upper surface of the flexible circuit (the Tefzel layer) and then pushes the switch pattern 57 against silver shorting dot 44 in recess 42, completing the electrical circuit. LEDs 58 and 59 are both illuminated, indicating too much brushing pressure is being applied to the teeth/gums. The arrangement/material (low friction) of the flexible circuit permits the normal back/forth movement of the brushhead during sensing of normal pressures on the brushhead.

As discussed above, the arrangement is such that a total force of approximately 150 grams produces the electrical contact between the shorting dot and switch pattern 57. However, it should be understood that if a different force was desired for a particular application, a different arrangement could be designed. When the circuit is complete, indicating that a pressure of at least 150 grams has been applied, the LEDs light, indicating that there is a pressure overload, i.e. that the desired upper limit of 150 grams has been exceeded.

The present invention, because of the rigid rear shield arrangement, with the brushhead moving toward the shield under pressure, provides a true indication of actual pressure on the brushhead, including pressure exerted by the cheek and tongue tissues (against the rear surface of shield 32) as well as pressure exerted by the user. The tissue pressure, acting on the rigid brush shield, tends to force the brushhead against the teeth. The pressure can be quite large when the brushhead is in the vicinity of the rear molars. The present invention takes the tissue pressure into account automatically. This accuracy in measuring a true "total" pressure is an important aspect of this invention. In some cases, it may even be necessary for the user to exert some force away from the teeth, in order to stay under the overload threshold, due to the tissue pressure.

Applicant is aware of alternatives to several of the structural elements discussed above. For instance, it is possible that the Tefzel portion of the flexible circuit 50 overlaying the area of the switch pattern could be eliminated. The nubbin cover 64 would then rub directly on the Mylar layer. The stainless steel nubbin wears equally well directly on a Mylar surface as on a Tefzel surface, although the Tefzel has a lower friction surface. In some cases, nubbin 64 may not be necessary.

Further, the breathing arrangement could include a small groove extending under the flex circuit to the rubber seal. A small hole would be made for this embodiment through or under the sealing rim of the rubber seal. The pressure of the seal would continue to maintain the circuit waterproof but would permit a slow air venting for the switch. A further alternative involving the flex circuit would be the use of an oleophobic membrane (such a membrane will not pass water or organic solvents), positioned with an adhesive capable of breathing over an opening in the flex circuit which is located over the vent chamber. This would permit the switch to be vented to the outside through the membrane and adapt to atmospheric changes yet prevent liquids from contacting the electrically conducting portion of the flex circuit.

Also, it should be understood that while the present invention includes a separate shorting dot in recess 42, which in combination with the switch pattern in the flex circuit results in the necessary electrical contact to complete the circuit, indicating that the maximum desired pressure has been exceeded, it is possible to have a flex circuit which might itself contain shorting circuitry designed to respond to a particular pressure to produce electrical contact. Hence, it should be understood that there are a variety of structural arrangements which can produce an electrical circuit connection in response to a particular pressure on the brushhead by the user, including force measuring means with a variable readout. This could include a number of different lights driven by appropriate logic circuits, indicating different levels of pressure, including inadequate pressure, acceptable pressure and various levels of unacceptable pressure. The structure, of course, must be calibrated to produce the desired electrical contact when the maximum desired force or pressure has been exceeded.

Figure 7A:
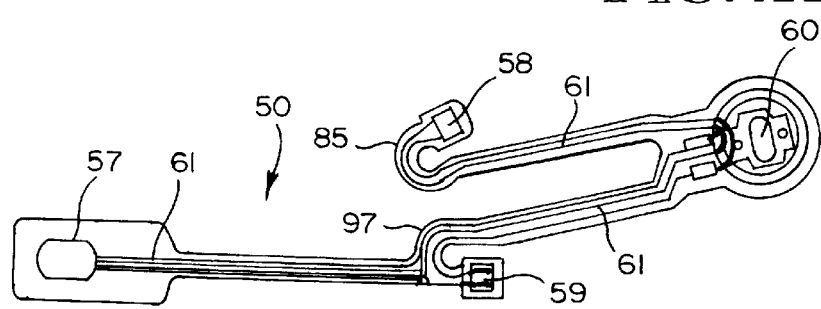
FIG. 7A is a plan view of a flexible switch circuit portion of the present invention with two light emitting diodes (LEDs).

Referring to FIGS. 7A and 7B, the electrical circuit portion of the flexible circuit comprises an interdigitated switch pattern 57 which forms the electrical contacts of the circuit and which is positioned directly over the electrically conducting shorting dot in recess 42 in the brush shield 32, a battery 60 which supplies power to the interdigitated switch pattern, two opposing LEDs 58 and 59, and the connecting members 61 which interconnect those elements. In the embodiment shown, the connecting elements are in the form of a silver ink printed circuit, although alternatively the circuit could be etched copper with soldered components, or in another alternative a hybrid arrangement, with silver ink for the switching pattern and etched copper in the remainder of the circuit. FIG. 7C shows an alternative flexible circuit using only one LED.

As indicated above, the electrically conducting circuit portions of the flexible circuit are mounted on the lower surface of the Mylar layer. The battery 60 and LED terminating sections are encapsulated with a waterproof sealant, while a dielectric material is printed over the silver or copper connecting lines 61, where the lines are not covered with PSA, to waterproof them. The dielectric sealant extends under an edge of the PSA at seal 30 and under the edge of the encapsulating material for the battery and the LED terminating sections. Thus, the electrically conducting portions of the flexible circuit are completely sealed, except for the area over the switch pattern 57.

The switch pattern is, as indicated above, a conventional interdigitated arrangement which, when there is no pressure applied on the switch pattern, is electrically open; however, once sufficient pressure is applied, a good electrical contact is made between the interdigitated elements of the switch pattern and the shorting dot 44, which completes the electrical circuit, lighting the two conventional LEDs 58 and 59 (or one LED, as the case may be). The arrangement of the interdigitated fingers can provide a somewhat varying connection depending on the amount of pressure applied. This could be used to produce a varying LED light level, giving an indication of variance in pressure applied.

The overall design of the flexible circuit shown in FIG. 7A is significant, in that it permits the flexible circuit to be readily folded and positioned in the brush housing, without producing significant stress on the adhesive bonds between the conductive circuit itself and the two (or one) LEDs. The LEDs of FIG. 7A are each at the ends of semi-circular portions 85, 97 of the electrical connecting circuit. Both semi-circular portions 85 and 97 connect to battery 60 via straight-line portions of connecting elements 61. In the alternative arrangement of FIG. 7C, only one LED 99 is used. Otherwise, the circuit remains the same. The interdigitated switch pattern is positioned a short distance (approximately two inches) from one of the LEDs, also via a straight-line portion of connecting elements 61, extending from the semi-circular portion 97 in the embodiment of FIG. 7A. The flexible circuit is folded into the housing and the interdigitated switch pattern 57 and surrounding portion of the flexible circuit is attached to the plastic shield by means of a pressure-sensitive adhesive.

Battery 60 in the embodiment shown is a lithium battery, which has a high internal impedance. The lithium battery eliminates the need for resistive circuit elements. The lithium battery provides substantially constant current over its entire life. As an alternative, alkaline batteries or other single cell batteries (without internal impedance) could be used, although this would require the use of resistive elements in the flex circuit so as to reduce the resulting current to permissible levels for the LEDs.

LEDs 58 and 59 are arranged so that they appear through the brushhead housing, 180° apart, on the top and bottom thereof. This position was the easiest to implement in the embodiment shown, and it may be easier to see the LEDs when they are lit in such an arrangement. The dome-shaped LEDs in the embodiment shown protrude through the flex circuit and into the openings made for them in the brush housing, thereby eliminating separate lenses for the LEDs. The LEDs are glued and sealed in place in the housing opening with a UV (ultraviolet) cured adhesive. As indicated above, however, one LED could also be used, mounted in a position which is easy for the user to see. Battery 60 is held in place by mating recesses in upper and lower halves 35, 37 of housing 31. The above is shown most clearly in FIG. 8.

An alternative to the mounting arrangement for the LEDs is a metal spring clip positioned over the LEDs. The clip would have barbed points that would be forced into the interior of the plastic walls of the brush housing to hold the LEDs firmly in place in their openings.

In the embodiment shown, the switching circuit is either on (the LEDs are lit, indicating excessive pressure) or off (the LEDs are not lit, indicating less than excessive pressure). It is possible, however, to provide a variable pressure reading, with either multiple separate pressure readings or a continuous pressure reading (with variable numbers). For instance, the embodiment shown with the interdigitated fingers can produce an increase in brightness of the LEDs as pressure increases, as indicated above. This pressure indicating range is made possible by the structure involving the rigid brush shield and the movable brushhead. Also, the variable pressure indicator could be used to indicate low pressure and a proper pressure as well as excessive pressure.

The present embodiment involves a sensor using physical contact between separate elements to establish the threshold indication of excessive pressure. However, using the fixed brush shield, non-contact sensors, such as strain gauges or MEMS sensors could be used between the movable brushhead and the adjacent rigid brush shield to determine pressure on the brushhead.

FIGS. 9 and 10 show an additional alternative for the indicator lights. Instead of one or two LEDs which are mounted so as to partially protrude through the housing to give a visual indication of excessive pressure, the alternative shown in FIGS. 9 and 10 utilizes a light block guide 102 along with a single LED 104 which is mounted centrally thereof. The light block guide 102 is made of a clear, light-transmitting plastic material having a central recess 106 in which an LED portion 104 of a flexible circuit is positioned. At the bottom of the recess 106, the light block guide 102 has an inverted "V" configuration portion 106 which reflects the light from the LED in two opposing directions to two wing-like portions 110, 112 which extend outwardly from the central recess 106 and are 180° apart. Each wing-like portion 110, 112, respectively, has a light-emitting section 114, 116 which in the embodiment shown is slightly convexly curved and approximately ⅜ inch long by ¹⁄₁₆ inch wide.

When the electrical circuit is closed and LED 104 is lit, the two light emitting sections 114, 116 also light, providing a significant visual indication of excessive pressure. This arrangement has some advantages in that the light-emitting sections 114, 116 are bigger than the LEDs. In addition, because only one LED is necessary, manufacture of the apparatus can be somewhat simplified. Further, with the simplified arrangement, it is easier to assemble the toothbrush, as the light block needs only to be positioned within the bottom portion of the housing and the LED portion of the flexible circuit then mounted into the center recess. The assembly would overall appear to be more reliable.

Although a preferred embodiment of the invention has been disclosed herein for illustration, it should be understood that various changes, modifications and substitutions may be incorporated in such embodiment without departing from the spirit of the inventions which is defined by the claims which follow.

What is claimed is:

1. A pressure overload indication system for power toothbrushes, comprising:
   a brushhead member having a mounting base for bristles which extend from one surface thereof and a pressure contact element which extends from an opposing surface of said mounting base;
   a substantially rigid brushhead shield member which is positioned apart from the pressure contact element when there is no pressure applied to the brushhead;
   electrical contact elements, mounted on the brushhead shield so that when no pressure is applied to the brushhead there is a first selected distance between the pressure contact element and a first electrical contact element and a second selected distance between the electrical contact elements, wherein the first electrical contact element is movable under pressure toward another electrical contact element, the electrical contact elements being part of a normally open electrical circuit which includes an indicator element; and
   a hinge-like member supporting the brushhead at an inboard end thereof which allows the brushhead to move toward the brushhead shield member when pressure is applied on the brushhead against the teeth, wherein the first and second selected distances are such that a predetermined pressure applied to the brushhead results in electrical contact between the electrical contact elements, closing the electrical circuit and activating the indicator element, indicating a pressure overload condition.

2. An apparatus of claim 1, wherein the apparatus is arranged and characterized such that the pressure applied on the brushhead includes pressure caused by cheek and tongue tissues of the user, acting against the brushhead shield.

3. An apparatus of claim 1, wherein the electrical contact elements and the pressure contact element are in alignment.

4. An apparatus of claim 1, wherein the electrical circuit includes a plurality of circuit elements, including a battery, a normally open switch pattern member, at least one visual indicator and electrical circuit means providing interconnection of the circuit elements.

5. An apparatus of claim 4, including a recess in a surface of the brushhead shield, wherein one electrical contact element is an electrically conducting member positioned in the recess, and wherein said switch pattern member overlays the recess so that pressure exerted by said pressure contact element on said switch pattern member brings said switch pattern member into electrical contact with said electrically conducting member, closing the electrical circuit and activating the indicator element.

6. An apparatus of claim 5, wherein the visual indicator is an LED.

7. An apparatus of claim 5, wherein the electrical circuit is mounted to a strip of plastic material and includes sealing means for the electrical circuit to prevent liquid from reaching the electrical circuit.

8. An apparatus of claim 5, wherein the visual indicator is a light block element mounted in the toothbrush so as to be visible to a user, the light block element being shaped and configured to reflect a source of light mounted thereto in two directions, into two separate illumination sections through which reflected light is visible to the user, wherein the source of light is activated when the electrical circuit is closed.

9. An apparatus of claim 5, wherein the electrical circuit includes two LEDs, which are positioned at the free ends, respectively, of half-circle portions of the electrical circuit.

10. An apparatus of claim 1, wherein the pressure contact element is a stainless steel nubbin, the nubbin having end portions which extend through openings in said mounting base.

11. An apparatus of claim 10, wherein the end portions are serrated so that a gripping relationship develops between the brushhead and the end portions.

12. An apparatus of claim 10, wherein the stainless steel nubbin includes a domed portion which contacts the electrical contact elements.

13. An apparatus of claim 5, including a second recess in the brush shield and a groove connecting the first recess with the second recess, the second recess acting as a vent chamber for the first recess to prevent pressure build-up in the first recess when the electrical contact elements close.

14. An apparatus of claim 7, including a groove which extends from the first recess past the sealing means to prevent pressure build-up in the first recess.

15. An apparatus of claim 5, including an oleophobic membrane located with the electrical circuit in such a position as to permit venting of pressure in the recess therethrough.

16. An apparatus of claim 5, wherein the electrically conducting member is at least one dot which includes a layer of electrically conducting silver ink on a top surface thereof.

17. An apparatus of claim 5, wherein the electrically conducting member is a silver ink dot printed in the recess.

18. An apparatus of claim 5, wherein the switch pattern member comprises an interdigitated finger pattern comprising two pattern portions, each of which is connected, respectively, to respective ends of the electrical circuit, wherein the interdigitated pattern portions are connected electrically and the electrical circuit closes accordingly when the interdigitated pattern portions are brought into physical contact with the electrically conducting member in the recess.

19. An apparatus of claim 7, wherein the pressure overload indication system is characterized such that brushhead movement is not significantly reduced when the pressure contact element is in contact with the closest electrical contact element for non-overload pressures.

20. An apparatus of claim 1, including means for indicating various pressure values, including inadequate pressure and proper pressure, in addition to excessive pressure.

21. A pressure overload indication system for power toothbrushes, comprising:
   a brushhead member having a mounting base for bristles which extend from one surface thereof;
   a substantially rigid brushhead shield member which is positioned apart from the brushhead member when there is no pressure applied to the brushhead;
   pressure sensing means between the brushhead member and the brushhead shield;
   a hinge-like member supporting the brushhead at an inboard end thereof which allows the brushhead to move toward the brushhead shield member when pressure is applied on the brushhead against the teeth, acting on the pressure sensing means; and
   wherein the pressure sensing means determines the pressure exerted on the brushhead; and
   means for indicating when the pressure sensed by the pressure sensing means exceeds a predetermined value.

22. An apparatus of claim 21, including means for indicating various pressure values, including inadequate pressure and proper pressure, in addition to excessive pressure.

23. An apparatus of claim 21, wherein the pressure sensing means is located near an outboard end of the brushhead shield, substantially directly away from the brushhead.

24. A pressure overload indication system for power toothbrushes, comprising:

a brushhead member having a mounting base for bristles which extend from one surface thereof and a pressure contact element which extends from an opposing surface of said mounting base;

a substantially rigid brushhead shield member which is positioned apart from the pressure contact element when there is no pressure applied to the brushhead;

electrical contact elements, mounted on the brushhead shield so that when no pressure is applied to the brushhead there is a selected distance between the electrical contact elements, wherein one electrical contact element is positioned between the pressure contact element and the other electrical contact element, wherein said one electrical contact element is movable under pressure toward said other electrical contact element, the electrical contact elements being part of a normally open electrical circuit which includes an indicator element; and a hinge-like member supporting the brushhead at an inboard end thereof which allows the brushhead to move toward the brushhead shield member when pressure is applied on the brushhead against the teeth, wherein a predetermined pressure applied to the brushhead results in electrical contact between the electrical contact elements, closing the electrical circuit and activating the indicator element, indicating a pressure overload condition.

25. An apparatus of claim 24, wherein the apparatus is arranged and characterized such that the pressure applied on the brushhead includes pressure caused by cheek and tongue tissues of the user, acting against the brushhead shield.

\* \* \* \* \*